United States Patent [19]

Morgan

[11] Patent Number: 4,738,142

[45] Date of Patent: * Apr. 19, 1988

[54] DIAGNOSTIC GRAIN PROBE

[76] Inventor: Dean Morgan, 4111 Adelphi La., Austin, Tex. 78727

[*] Notice: The portion of the term of this patent subsequent to Sep. 19, 2004 has been disclaimed.

[21] Appl. No.: 614,122

[22] Filed: May 25, 1984

[51] Int. Cl.[4] .......................... G01N 1/16; G01N 1/08
[52] U.S. Cl. .................................. 73/864.64; 374/157
[58] Field of Search ........................ 73/864.64, 864.43; 374/157

[56] References Cited

U.S. PATENT DOCUMENTS

| | | | |
|---|---|---|---|
| 1,229,273 | 6/1917 | James et al. | 73/864.61 |
| 2,184,472 | 12/1939 | Sand | 73/864.64 X |
| 2,331,227 | 10/1943 | Proudlock | 374/157 |
| 3,065,637 | 11/1962 | Landes | 73/864.64 |
| 3,091,968 | 6/1963 | Platzer | 73/864.64 X |
| 3,192,773 | 7/1963 | Wilson | 73/864.64 |
| 3,738,176 | 6/1973 | Kerfoot | 73/864.64 |

Primary Examiner—Stewart J. Levy
Assistant Examiner—Tom Noland

[57] ABSTRACT

Apparatus for the simultaneous and uniform sampling of grain and recording of temperature from various predetermined locations within a grain storage facility. The apparatus consists of a drive section made of high strength material, such as steel, to which is attached a downwardly spiraling flight which enables the device to be driven into or out of stored grain. Attached above the drive section are sampling sections of equal length made of a light strong material, such as aluminum. Each of the sample sections has a sampling gate, which when opened receives samples of grain from each of the predetermined locations within the grain storage facility. Additionally, the device incorporates a thermometer within each of these sampling sections which is attached and secured in position by an alignment bar which additionally serves to positively join each of the sections to the other. Below the drive section is attached a shorter sampling section which comprises the tip of the probe. This tip section also has a sample gate and a thermometer, thereby providing the ability to obtain a sample and a temperature reading from very close to the floor of the storage unit. Further, the sampling tip section has a rounded point to help prevent damage to the floor of the storage unit. Sample gates are opened by first removing the drive adapter from the top sampling section, thereby exposing the top of an alignment bar which is square in shape. The gate-actuating tool is placed over the top of the alignment bar and, when rotated a quarter turn in either direction, simultaneously opens the gates in all sections of the probe. After the sample is obtained, returning the gate-actuating tool to its original position closes the gates. As the probe is withdrawn from the grain storage facility a detent release tool is used to depress the detents on the alignment bars and thereby separate each of the sections.

5 Claims, 1 Drawing Sheet

DIAGNOSTIC GRAIN PROBE

BACKGROUND OF THE INVENTION

This invention pertains to a device which is designed to provide regular and factual information concerning the status of stored grain. The gist of the invention is a sectional probe device composed primarily of standard sampling sections, a drive section and a tip section with gates within those sections to catch and hold samples of grain and to record the temperature of the captured grain samples on a thermometer. The sections are aligned and held together by an alignment bar which positively joins separate sections by the use of detent buttons. Additionally, the alignment bar is designed to provide a space to locate and attach the thermometer in each section. The thermometers are shielded and may be used in any or all sections of the probe. Further, the drive section is a standard sampling section modified by the addition of a welded, downwardly spiraling flight which enables the probe to be driven into the grain. Below the drive section is attached a small sampling section called the "tip" section. This tip section is shorter than the standard section and adapted with a rounded end so that grain may be penetrated but the bottom of the grain storage facility will not be punctured. Additionally, the tip section is also designed to include sampling gates and a thermometer so that a sample close to the bottom of the grain storage facility may be obtained. The invention also includes a drive adapter which is inserted into the top of each section as they are sequentially driven into the grain. The drive adapter has a tapered hexagon shaped tip which allows fast, easy coupling with a drive unit utilized to rotate the probe as it is driven into or out of grain. Further, the device utilizes a gate-actuating tool which fits over the squared alignment bar once the drive adapter is removed. When the gate-actuating tool is turned a quarter turn in either direction all the gates in the probe are opened and samples are taken. When the tool is returned to its original position the samples are secured within the probe as it was taken at each depth within the grain. Finally, the device utilizes a detent release tool designed to depress the detent buttons securing the individual sections together so that the sections may be separated as the probe is withdrawn from the grain. The detent release tool is curved to fit the hand of the probe operator.

DESCRIPTION OF PRIOR ART

While there are numerous types and designs of grain testing devices, to the best of this inventor's knowledge, there has never been an invention such as this designed to simultaneously obtain several samples of grain at various depths and accurately record the temperature of the grain at each depth with a probe capable of being driven into grain masses up to 100-plus feet in depth and return the individual samples to the surface for further investigation. Prior grain testing devices were designed to be continuously and constantly pushed into grain to a depth that was shallow in comparison to this device. Further, previous devices, once pushed as far into the grain as was possible, could not be pulled up to a different depth without lifting the top of the sampling device and filling the sampler with grain. These devices typically could be pushed no more than 15 to 20 feet into the grain and could only provide the operator with one sample at one place. Additionally, these hand driven devices were time consuming to use. Further, these devices have typically been made of brass which conducted heat into the sample and provided false readings on the thermometer, if one was provided.

Other prior inventions consisted of temperature cables which were designed to be horizontally introduced into the grain mass to provide temperatures at different levels. These devices, if inserted prior to loading the facility with grain, would typically break off or bend down to the floor as grain was loaded. After grain was loaded, the insertion of these devices was difficult or impossible. Additionally, once the temperature cable was inserted, it was difficult or impossible to determine if the temperature readout was accurate or if the device was damaged in some respect. Additionally, these temperature sensing cables could not provide samples of the material sensed so that it was impossible to determine whether a hot spot was caused by moisture or insects or some other abnormality.

Other temperature sensing devices are manually pushed into the grain and in some cases an attempt is made to pull air from within the grain over the temperature sensing device for an accurate reading of the temperature of the grain at a specific location. These devices, however, suffer in that they generally get plugged up with grain in the process of attempting to draw air from within the grain itself, and further, they are limited in that they are manual insertion devices and can only be inserted to a depth of approximately 15 feet.

SUMMARY OF THE INVENTION

This invention consists of a diagnostic grain probe made up of several probe sections. The probe sections interlock and are kept in place by an alignment bar which serves the dual purpose of securing each section to the other and also providing a place to secure a thermometer within each of the sections of the probe. The drive section of the probe is equipped with a downwardly slanting spiral flight, which, when the shaft is rotated, drives the probe into or out of the grain. Further, each section of the probe has a grain sampling gate which may be simultaneously opened and closed by a manual gate-actuating tool from the surface of the grain facility. A shorter tip section is attached beneath the drive section of the device to allow sampling of the grain to within 8 inches of the bottom of the grain storage facility as well as to allow for a temperature reading at that depth.

While this device is particularly well suited for application to grain sampling and temperature readouts in grain storage facilities to depths of up to 100-plus feet, it is anticipated that other practical uses of the invention are readily available. That is, the device can be employed as a means to insert vertical temperature sensing devices or adapted to take liquid, solid, or gas insecticides to the exact location of the infestation for spot treating of infested grain. Further, application can be envisioned for the modification of the device to provide for remote sensing along each section of the device for temperatures without necessitating the withdrawal of the probe to read each individual thermometer.

Characteristics that further describe this device are that it is self-propelled and as designed allows for an accurate deep penetration of a grain storage facility. Further, the device is insulated by its double wall construction, thereby insuring that sample readings are not influenced by different temperatures while the device is being inserted or withdrawn. Additionally, the functional utility of the device is enhanced by the fact that it is to be made of aluminum or the like with the exception of the drive section which is to be made of a high strength material such as steel. This almost all aluminum construction reduces the chance of sparks being generated by the device itself. Further, the tip of the device is rounded, as opposed to pointed as in previous inventions, thereby helping to ensure that the device itself does not damage the floor of the grain facility. Further, the device combines the advantage of being able to take temperatures at several predetermined locations while at the same time having the ability to sample grain from those same locations. Further, it is apparent that the device can be used not only to measure temperature and sample grain within the storage facility but may also be used to insert permanent temperature sensing devices, be fitted with electrical sensing devices that can provide instantaneous readouts of moisture and temperature at multiple locations within the facility, and also be fitted with an adapter to spot treat infestations with liquid, solid, or gas insecticides.

The object of the invention is to provide a diagnostic grain probe that insures that accurate grain and temperature samples from predetermined locations within a grain storage facility may be obtained rapidly and repeatedly in a short period of time.

BRIEF DESCRIPTIONS OF THE DRAWINGS

For a description of the construction and operation of the device of this invention, reference is made to the attached drawings, and identical reference characters will be utilized to refer to an identical or equivalent structure throughout the various views in the following detailed description.

DETAILED DESCRIPTION

Figure 1:
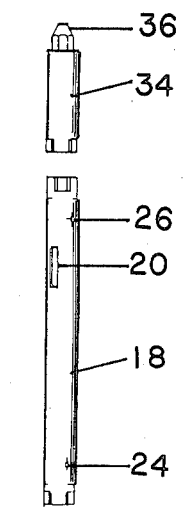
FIG. 1 is an exploded sectional view of the device in total.
Figure 1:
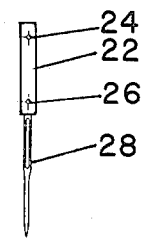
Figure 1:
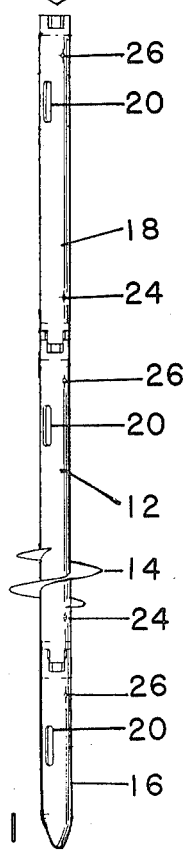

Referring to FIG. 1, 10 denotes the invention itself consisting of drive section 12, attached to which is downwardly spiraling flight 14 and below said drive section 12 is attached tip section 16. Above said drive section 12 is any number of standard sampling sections 18. Each standard sampling section 18 as well as the drive section 12 and tip section 16 contain a sampling gate 20. All of these sections are connected and held together by alignment bars 22 which have detents 24 and 26 oppositely positioned at each end of said alignment bar 22. In addition to securing each section to the other, alignment bar 22 also provides a place to secure thermometers 28. Said thermometers are screwably attached to alignment bars 22. Drive adapter 30 inserts into the top of each section for coupling to the drive unit, not shown. The tapered tip 32 allows for quick coupling with the drive unit and drive adapter 30 keeps sample gates 20 closed during insertion and withdrawal of the device 10 from a grain storage facility.

Figure 2:
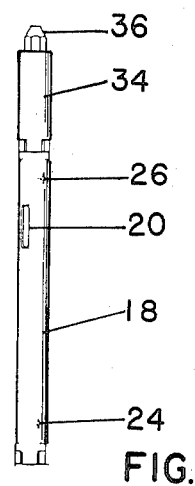
FIG. 2 is the drive adapter in plan view.
Figure 3:
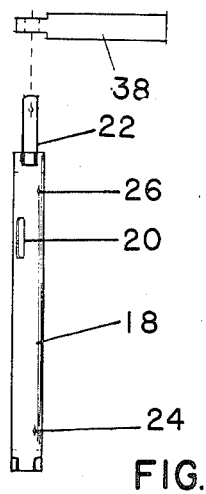
FIG. 3 is the gate-actuating tool shown in plan view.

Dive adapter 30 is more fully described in FIG. 2 where it is shown in plan view. FIG. 3 illustrates gate-actuating tool 34 which is used after drive adapter 30 is removed, by placing gate-actuating tool 34 over the end of the top-most alignment bar 22 attached to the top-most standard sampling section 18. Said gate-actuating tool 34 is then rotated a quarter turn in either direction and thereby opens sample gates 20 in all the probe sections. Returning the gate-actuating tool 34 to its original location closes all sample gates 20 in each of the probe sections.

As previously stated, invention 10 is constructed of double walls. That is, instead of one wall as disclosed in previous devices, this invention has two walls. The outer wall is illustrated in the figures as sections 18. FIG. 1 illustrates the interlocking of section 18 with drive section 12 where the T shaped joints fit into the U shaped slots at the bottom of section 18 and the top of drive section 12 respectively. At the very top of FIG. 1, drive adapter 30 is shown poised in position to be interlocked with outer section 18. Referring to FIG. 2, it is shown and illustrated that drive adapter 30 has interlocked with section 18 by means of the downward extending T portion of the bottom of drive adapter 30 with the upward extending U section of the top of section 18. As is demonstrated by these figures, torque is transmitted through drive adapter 30 to the outer section 18 of the double walled invention 10. When drive adapter 30 is removed, it reveals the upper most portion of the top most alignment bar 22. It is clear from the discussion and the illustrations in FIG. 1, 2 and 3 that drive adapter 30 fits over connector 22 but only engages section 18 and not alignment bar 22. FIG. 3 illustrates gate actuating tool 34, which slips over the end of alignment bar 22 and engages alignment bar 22 as discussed. Rotating the gate actuating tool 34 a quarter of a turn in either direction opens sample gates 20 by the obvious means of rotating the inner tube of the previously described double walled invention 10. There is no other way to provide a double walled insulation and a means for opening all sample gates 20 in all the probe sections 18 as described and illustrated other than to have the inner wall of the double wall construction be connected by the alignment bars 22 as described and illustrated. Because drive adapter 30 fits over alignment bar 22 and into outer wall section 18 but does not engage alignment bar 22, as illustrated in FIGS. 1 and 2, no torque is transmitted to the inner wall while the device is driven into or out of the grain. Likewise, because of the double wall construction, by utilizing gate actuating tool 34, which slips over alignment bar 22, which is connected to the inner wall sections of the double walled invention 10, positive opening and closing of the gates 20 is provided.

Figure 4:
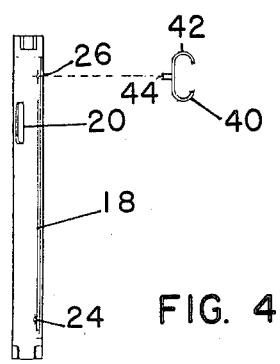
FIG. 4 is the detent release tool shown in plan view.

FIG. 4 illustrates the detent release tool 36 designed with a curved handle 38 so as to be held easily by the grain probe operator for use in depressing detent buttons 24 and 26 on alignment bars 22 with detent depressor 40.

Thus, according to this invention, simultaneous grain sampling and temperature recording may be obtained deep within a grain storage facility by utilization of the above-described diagnostic grain probe. The device is lighweight, easy to assemble and maintain, and does not suffer from any of the other debilitating defects of previous grain storage sampling devices.

While the invention has been described in connection with the preferred embodiment, that is its utilization as a grain storage sampling and temperature sensing device, the inventor does not intend to limit the invention to the particular form set forth but, on the contrary, it is intended to cover alternatives, modifications, and equivalents as may be included within the spirit and scope of the invention as defined by the appended claims.

What is claimed is:

1. An apparatus for grain testing comprising:
   (a) a double walled probe in a plurality of sections;
   (b) a removably attachable alignment bar means joining said sections; and
   (c) a removably attachable drive adapter means for driving said sections into and out of a mass of grain to collect a sample therefrom for testing, wherein said double walled probe in a plurality of sections includes: an outer wall section with an opening in it to receive a grain sample portion and with notches that interlock with other outer wall sections; each outer wall section containing an inner wall section with an opening in it to receive said grain sample poriton and which provides a double wall insulation, wherein said removably attachable alignment bar means joining said sections includes: two detention means positioned adjacent to opposite ends thereof and that detachably secure said inner wall sections to each other so that when said alignment bar means is rotated, all of said inner sections rotate together; and a shielded thermometer inserted within said alignment bar means readable when said opening in said outer and inner sections are aligned, and a sensing end extending down into one of said inner wall sections, and wherein said removably attachable drive adapter means includes; a lower poriton that fits non-engagably over said alignment bar means and which is removably engagable with said notches in said outer wall sections so that any force from said adapter means is transmitted to said outer wall sections; and an upper portion with a tapered tip to readily receive a driving means to turn said drive adapter.

2. An apparatus for grain testing comprising:
   (a) an outer wall section with an opening in it to receive a grain sample poriton and with notches that interlock with other outer wall sections;
   (b) each outer wall section containing an inner wall section with an opening in it to receive said grain sample portion and which provides a double wall insulation;
   (c) a removably attachable alignment bar with two detention means positioned adjacent to opposite ends thereof and that detachably secure inner wall sections to each other so that when one said alignment bar is rotated all of said inner sections rotate together;
   (d) a shielded thermometer inserted within said alignment bar readable when said openings in said outer and inner sections are aligned, with a sensing end extending down into one of said inner sections;
   (e) a removably attachable drive adapter means with a lower portion that fits non-engagably over said alignment bar and which is removably engagable with said notches in said outer wall sections so that any force from said adapter means is transmitted to said outer wall sections; and
   (f) an upper poriton of said drive adapter means with a tapered tip to readily receive a driving means to turn said drive adapter means.

3. The grain testing apparatus of claim 2 further comprising a short sampling tip section with a rounded point to allow sampling at or near the bottom of a grain storage facility with less risk of punching a hole in the bottom of said facility.

4. A method for testing grain comprising the steps of:
   (a) providing a plurality of outer wall sections with openings in them to receive grain sample poritons and with notches in both ends of said outer wall section that interlock with other outer wall sections;
   (b) inserting inner wall secitons within said outer wall sections with openings in said inner wall sections to receive said grain sample poritons and thereby providing a double wall insulation;
   (c) detachably securing a removably attachable alignment bar means with two oppositely positioned detention means to one of said inner wall sections so that when said alignment bar means is rotated all of said inner sections rotate together;
   (d) inserting a shielded thermometer within said alignment bar means readable when said openings in said outer and inner sections are aligned, with a sensing end extending down into one of said inner sections;
   (e) providing a removably attachable drive adapter means with a lower poriton fits non-engagably over said alignment bar means and which is removably engagable with one of said notches in one of said outer wall sections so that any force in said adapter means is transmitted to said outer wall sections; and
   (f) tapering the tip of the upper poriton of said removably attachable drive adapter means so that it readily receives a driving means for turning said drive adapter means.

5. The method for testing grain as recited in claim 4 further comprising the step of attaching a short sampling tip section with a rounded point to allow sampling at or near the bottom of a grain storage facility with less risk of punching a hole in said bottom of said facility.

* * * * *